United States Patent [19]

Bryan et al.

[11] Patent Number: 5,284,765
[45] Date of Patent: Feb. 8, 1994

[54] METHOD OF DIRECTIONALLY ORIENTING PLANT EMBRYOS

[75] Inventors: Curtis A. Bryan; William C. Carlson, both of Olympia; Michael K. McKinnis, Chehalis, all of Wash.

[73] Assignee: Weyerhaeuser Company, Tacoma, Wash.

[21] Appl. No.: 865,390

[22] Filed: Apr. 8, 1992

[51] Int. Cl.$^5$ .................. C12N 5/00; C12N 5/02; A01C 1/00; A01C 1/06
[52] U.S. Cl. .................. 435/240.4; 435/240.46; 435/240.54; 47/58; 47/57.6
[58] Field of Search .......... 435/240.4, 240.46, 240.54; 47/57.601, 58.27, 58.01, 58.16, 58.05, 57.601

[56] References Cited

U.S. PATENT DOCUMENTS 4,467,560  8/1984  Simäk .................. 47/58.27

FOREIGN PATENT DOCUMENTS

WO91/00781  1/1991  PCT Int'l Appl. .

OTHER PUBLICATIONS

Levin et al., Bio/Technology, vol. 6, pp. 1035–1040 (Sep. 1988).
Gray et al., Critical Reviews in Plant Science, 10(1) pp. 33–61 (1991).
Gray et al., In Vitro Cell & Dev. Biology, 23(1), pp. 29–33 (Jan. 1987).
Kim, Yong-Hwan, C. C. Velho, and J. Janick. Separation of somatic embryo stages by layered sucrose density gradient. HortScience, Programs and Abstracts (suppl.), p. 137 (1989).
Velho, C. C., Y. Saranga, and J. Janick. Density separation of zygotic and somatic embryos. HortScience, 25 (9): 1120 (1990). (Paper delivered Am. Soc. of Hort. Sci. Nov. 4–8, 1990, Tucson, Ariz.

Primary Examiner—Douglas W. Robinson
Assistant Examiner—Susan M. Weber

[57] ABSTRACT

The invention is a method of ordering plant embryos so that a specified end of the embryo is always oriented in a predetermined direction. The embryos are preferably first fairly rapidly desiccated to about 15% moisture content. They are then suspended in a benign liquid flotation medium having a density in the range of about 1.059–1.104 g/cm$^3$. The density must be adjusted empirically so that a predominant number of viable embryos will float and nonviable embryos will sink. In at least the case of conifer somatic embryos, they will float with the end bearing the latent cotyledons upward. After sufficient separation time in the flotation medium the oriented embryos are swept by a flowing liquid stream into a conduit. They enter cotyledon end first and are then carried to a delivery point without losing that orientation. Here they are separated from the transporting medium. The embryos, still positioned cotyledon end first, may then be picked up by robotic or other means for further processing, such as insertion into an artificial seed.

23 Claims, 3 Drawing Sheets

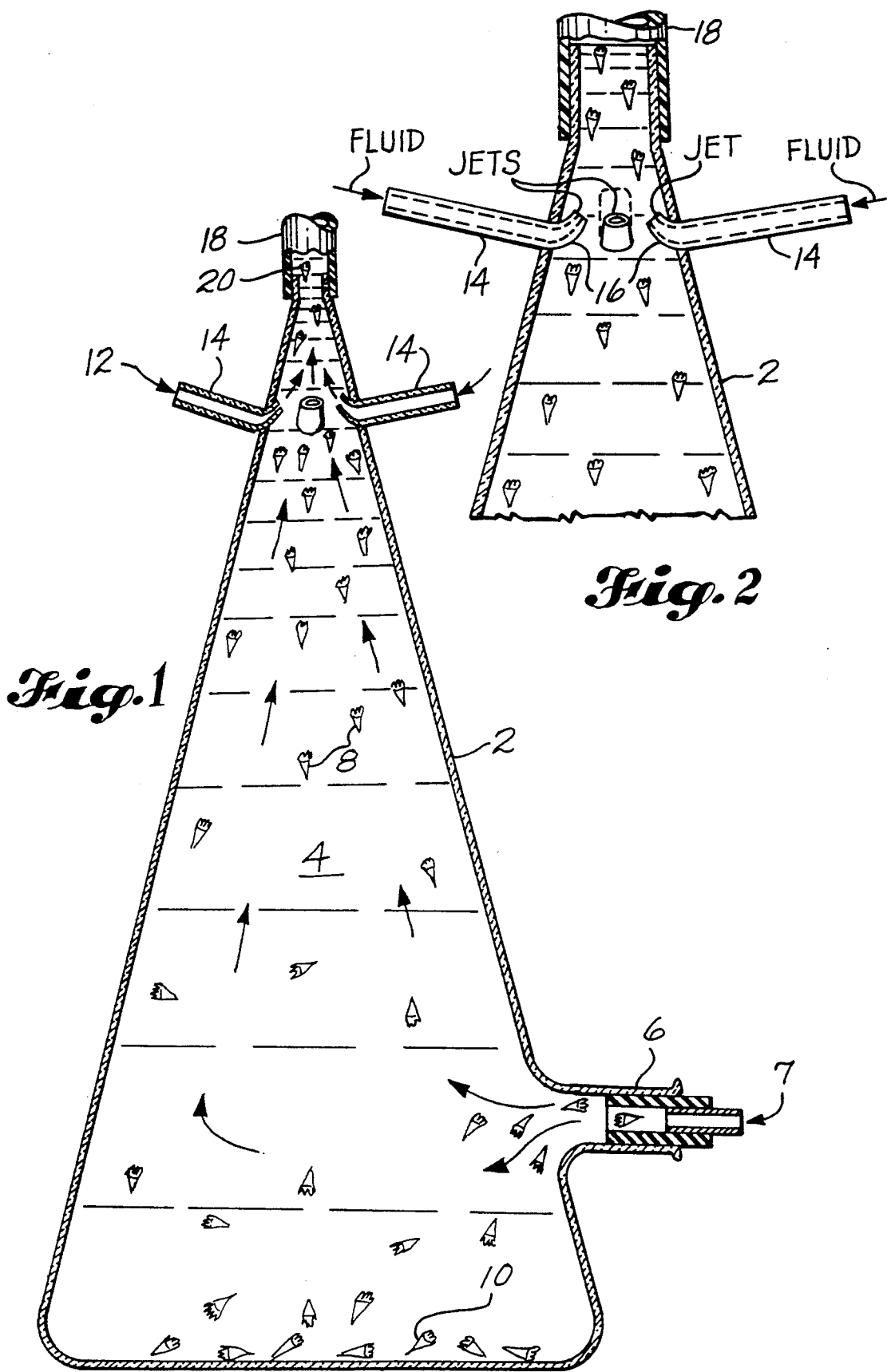

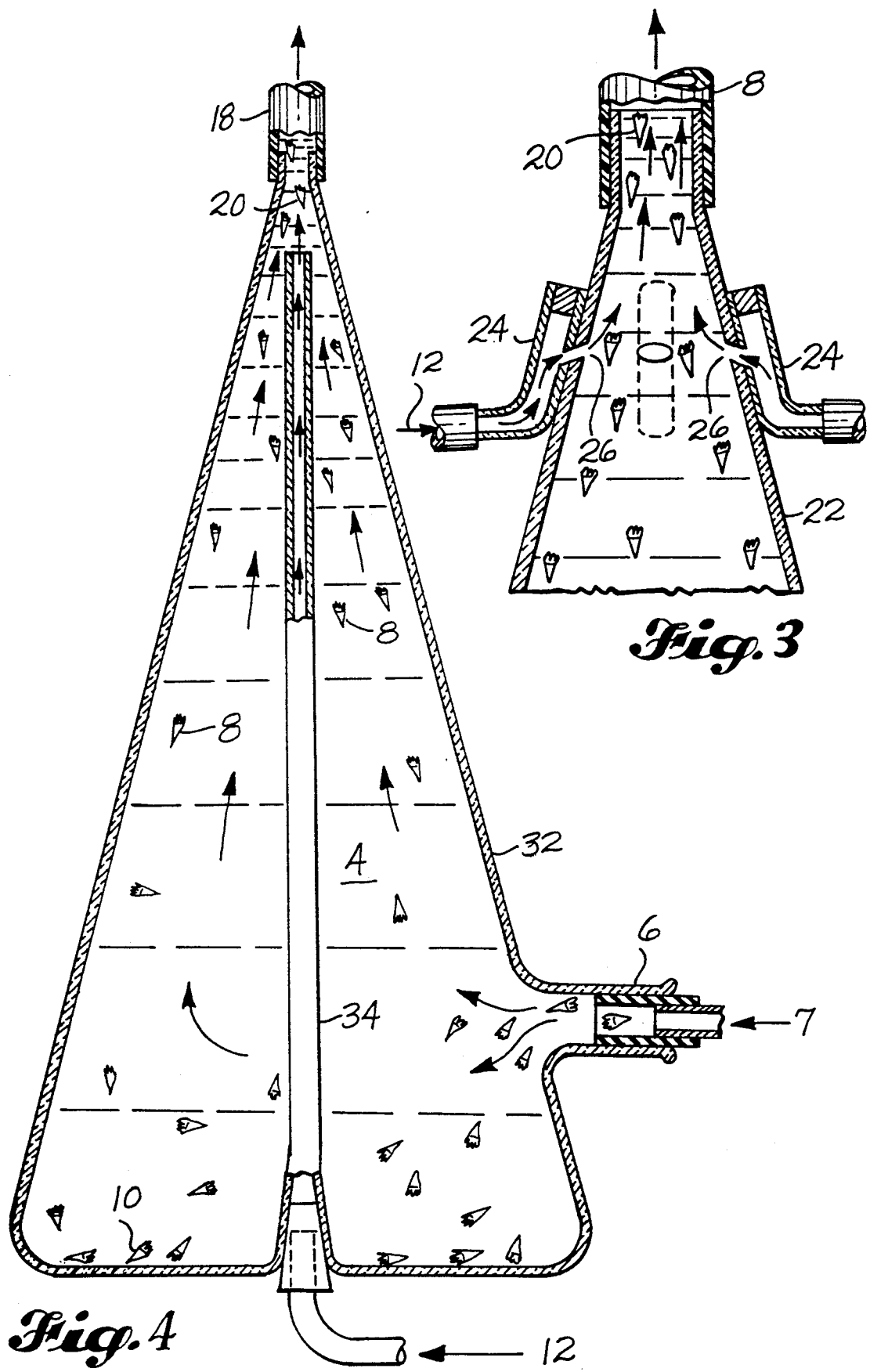

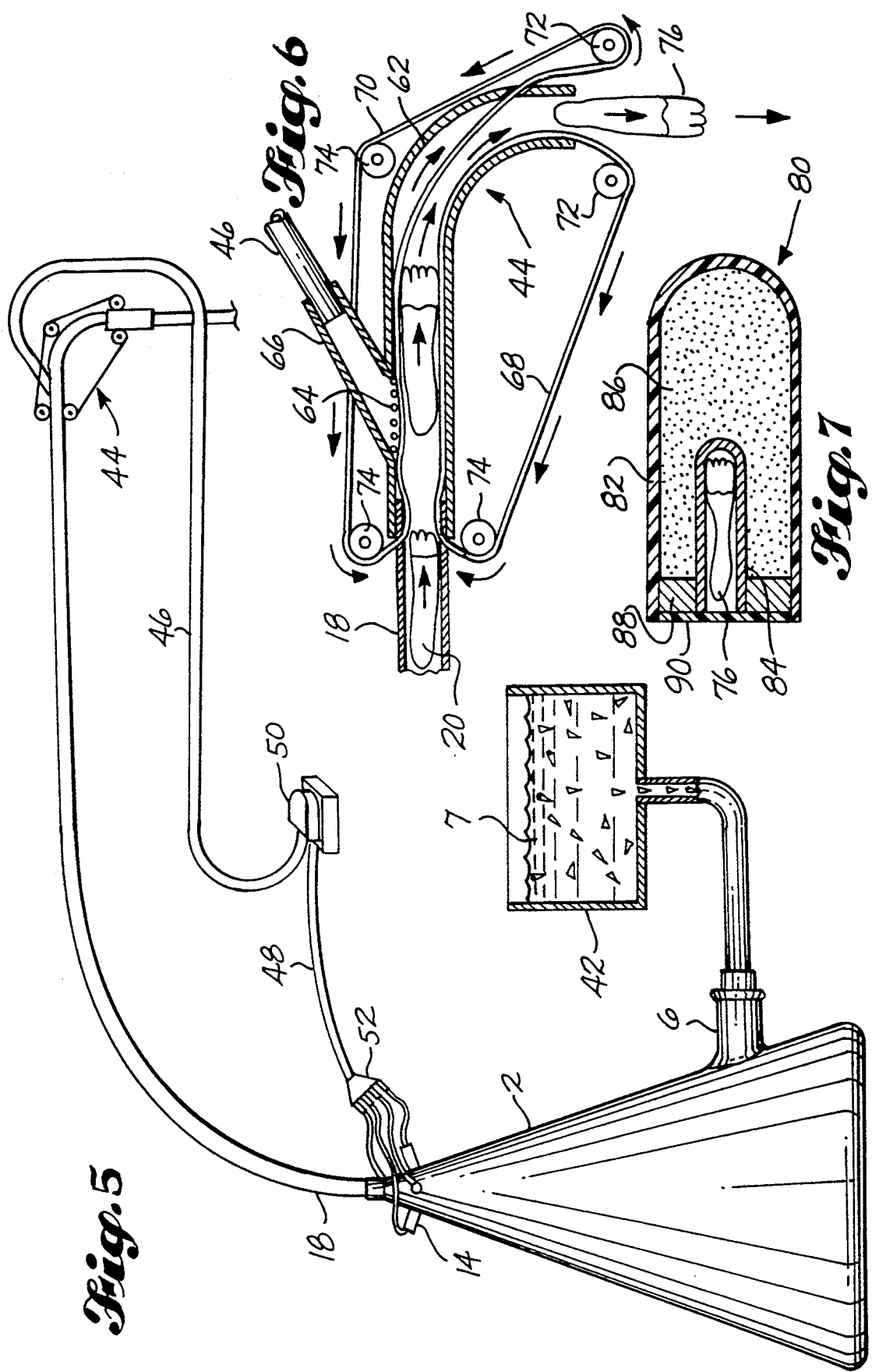

METHOD OF DIRECTIONALLY ORIENTING PLANT EMBRYOS

BACKGROUND OF THE INVENTION

The present invention is directed to a method of ordering plant embryos so that a specified end is always oriented in a given direction. The invention is also concerned with a method of separating viable from nonviable conifer somatic embryos and properly orienting the viable embryos for insertion into artificial seeds.

Reliable methods have now been developed for large scale production of plant somatic embryos of a large number of species using the techniques of tissue culture. In recent years much effort has been directed to development of techniques for embryogenesis of important conifer species. U.S. Pat. Nos. 4,957,866, 5,034,326, and 5,036,007 are exemplary of such methods. The work described in these patents has concentrated effort in particular on the commercially important United States species, loblolly pine *Pinus taeda* L. and Douglas-fir *Pseudotsuga menziesii* (Mirb.) Franco, and the similarly important European species, Norway spruce *Picea abies* (L.) Karst.

In culture the embryos are developed to a stage similar to the natural zygotic embryos occurring in mature seeds. For conifers these are very small, those for the species noted above falling in a range of about 2-4 mm in length. Embryos have a bipolar form which anticipates the ultimate plant. One end has a latent radicle or root and the other a whorl of tiny structures that will become the cotyledons of the germinated seed. The cotyledons, or seed leaves, are the first chlorophyll bearing organs and, in a natural seed, take over from the endosperm the job of providing nutrients to the newly germinated plant. The latent cotyledons look somewhat like a tiny crown situated at one end of the embryos.

Since somatic embryos lack the endosperm of the natural seed, some other means must be found to provide nutrients to the embryo at the time of germination. Various methods are available to accomplish this. The embryos may be placed on a solid germination medium containing the necessary carbohydrate and other nutrients, as described in any of the above patents. They may also be placed on a growing medium, or synthetic soil, which is saturated with an appropriate nutrient solution. In both of these cases sterility must be maintained until after the resulting plantlet is well established.

A preferred method of germinating a somatic embryo is to incorporate it into an artificial seed containing the essential nutrients. In essence, the artificial seed replaces the seed coat and endosperm of the natural seed. This method has the advantage that the embryos can be outplanted into a nursery bed in essentially the same manner as a natural seed.

A number of versions of artificial seeds have been described in the patent literature of the past half decade. Examples are U.S. Pat. Nos. 4,562,663; 4,583,320; 4,615,141; 4,715,143; 4,777,762; 4,779,376; and 4,780,987 and Canadian Patent 1,241,552. Most of these are variations on the theme of completely encapsulating a somatic embryo within a hydrophilic gel. The gel may be based on a material such as sodium alginate which can then be insolubilized on only the surface or throughout by cation exchange with a material such as calcium chloride. By insolubilizing at least the surface the resulting artificial seed can be more readily handled.

In two of the above noted artificial seed patents, U.S. Pat. Nos. 4,615,141 and 4,777,762, the embryos are partially or completely dehydrated in the process. By completely dehydrated is meant desiccated to a moisture content in equilibrium with normal ambient room conditions.

Despite the significant amount of work that has already been done, none of the above proposed artificial seed structures has proved suitable for conifer embryos. Germination has been low when the embryo is completely enclosed within the gel droplet. A major advance in artificial seed construction is reported in U.S. patent application Ser. No. 604,656, filed Oct. 26, 1990, and commonly assigned with the present invention. In this improvement, the gel serving as the endosperm contains an oxygen carrier and is heavily oxygenated at the time of formation. Artificial seeds made by the procedures described therein, using conifer embryos, have shown high percentages of normal germination when placed on soil.

One problem to be dealt with in making any of the artificial seeds described above is insertion of the somatic embryos. In most of the issued patents the embryos are merely suspended in the gel former while in a fluid state. This is dispensed in a dropwise fashion with each drop presumably containing a single embryo. This fond hope has not been found to be the case in reality. Many of the droplets contained no embryos while others contained multiple embryos.

Another problem is the variation in embryo maturity typical in tissue cultures of somatic embryos. Some embryos are at a fully mature stage while others have not developed as well. The less well developed embryos will seldom germinate into a normal plantlet. The usual solution to this problem has been a tedious hand selection. More recently a technical paper was presented that describes separation of loblolly pine zygotic embryos and celery somatic embryos by maturity using sucrose solutions having varying density gradients (Velho, Saranga and Janick. Density separation of zygotic and somatic embryos. Abstract of paper given at the 87th Annual Meeting of the American Society of Horticultural Science, Tucson, Ariz., Nov. 4-8, 1990.) In the case of loblolly pine embryos, density declined during development to a relatively constant level of 1.031 g/mL on the 49th day after fertilization. As a corollary of this observation, density was seen to be inversely proportional to embryo length. In the case of celery embryos, those classified as mature and overmature showed the best conversion to normal seedlings after desiccation for 48 hours at 90% R.H. The Abstract was unclear as to whether desiccation followed density gradient separation or was carried out on hand selected embryos not subject to this treatment.

Published International Application WO 91/00781 describes a procedure and apparatus for separating cells such as plant embryos from culture medium. This employs a scanner to identify and determine location of the desired cell and a pipetting mechanism to remove them.

The preferred form of artificial seed described in the above noted patent application is far more sophisticated in construction than those using simple gel droplets. It requires insertion of the embryo, cotyledon end first, into a thin moisture pervious tube surrounded by a nutrient gel enclosed within an outer capsule which provides the mechanical equivalent of a seed coat. The tube into which the embryo is inserted is barely larger in diameter than the embryo itself. If an economical production rate is to be obtained this process must be mechanized as much as possible. The present invention is directed to a method of delivering viable embryos, oriented cotyledon end first, to a seed assembly point. No additional sorting or orientation is required. From the delivery location the embryos may be handled by robotic or other means for insertion into the inner tube of an artificial seed of the type noted above.

SUMMARY OF THE INVENTION

The present invention is concerned with the orientation of plant embryos so that a specified end is essentially always oriented in the same direction at a selected location in space. It is particularly directed to the orientation of conifer somatic embryos for placement in artificial seeds.

The separation of plant embryos according to development maturity has already been noted. The method described uses a stratified aqueous medium having defined density gradients. Not surprisingly, germination success was greater when more mature embryos were selected.

It has now been noted by the present inventors that conifer embryos, when floated in a liquid of slightly greater density than that of viable mature embryos, will almost invariably float with the cotyledon end upward and the radicle end pointing down. This effect was quite unexpected. The invention now to be described makes use of this effect to achieve proper orientation of the embryos as they are taken up for placement in artificial seeds or used in some other application where a specific orientation is necessary.

The embryos are first introduced into an aqueous flotation medium held in a containment vessel. This flotation medium is of necessity a nonphytotoxic solution of a density slightly higher than that of the embryos to be selected. By precise control of flotation medium density it is possible to separate the embryos into essentially viable and nonviable groups. The viable embryos will float and the nonviable embryos will sink. By viable is meant embryos that have a high likelihood of germinating into normal plantlets. The flotation medium is of essentially uniform density throughout. A density gradient within the medium is not generally desirable. It is essential that turbulence within the flotation medium should be minimized and any flow should be of the laminar type. The embryos are retained in the flotation medium for a sufficient time to permit the viable embryos to float from the lower region of the medium, where they are introduced, to an upper region where they can be conveniently removed.

After reaching the upper portion of the flotation medium, the embryos are captured in a flowing fluid transport medium of increased velocity in a manner so that they are swept cotyledon end first into a small diameter conduit. The conduit diameter is preferably of sufficient diameter so that the embryos can be transported without undue friction but small enough so that the embryos cannot turn end-for-end. This helps to maintain the cotyledon end forward orientation. The embryos may be transported for some distance in the conduit to a delivery point. Here they are separated from the transporting fluid in a manner so that the cotyledon end first orientation is preserved. From this point they may be handled by robotic or other means for insertion into artificial seeds or placement on some type of germination substrate.

Preferably the containment vessel for the flotation medium is of gradually decreasing crosssectional area from bottom to top. This will increase the concentration of embryos per unit volume of solution as they approach the top of the containment vessel and facilitate removal. The containment vessel is most preferably of conical configuration although other forms are acceptable.

A preferred method of introduction of the embryos into the containment vessel is in suspension in an aqueous medium of very similar or identical composition and density to that of the flotation medium. This may be done in either a batchwise or continuous fashion. In the later case the suspended embryos must be introduced in such a manner that no appreciable turbulence is created in the flotation zone. Those embryos that sink; i.e., those that presumably are nonviable, may be withdrawn from the bottom of the containment vessel in either a continuous of batchwise fashion. In the case of continuous embryo introduction, the flow velocity in the upper part of the vessel will increase as a result of the decreasing crossectional area. This velocity increase should not be so great as to cause turbulent flow.

The floating embryos may conveniently be captured from the upper region of the flotation medium by introducing a moving stream of fluid transporting medium adjacent the top of the containment vessel. From here they are swept into the transport conduit without loss of orientation. In the case of a conical containment vessel the moving fluid stream may either be introduced around the periphery in some symmetrical manner or it may be introduced axially. In either case it should be directed upwardly; i.e., in the direction of travel of the rising embryos. For containment vessels of other than conical configuration different arrangements utilizing differential flow velocities may be employed. Preferably the transporting medium will also be of similar or identical composition and density to the flotation medium in the containment vessel. This enables this fluid to be recycled as embryo introduction medium or transporting medium or otherwise reused as long as it can be protected from entry of pathogens.

At the downstream end of the transport conduit the embryos are separated from the transport fluid for further processing. This can be done in a number of ways which are not the subject of the present invention. One such way is by catching the embryos on a moving belt mechanism which allows the transport fluid to drain from the embryos.

Increased discrimination between viable and nonviable embryos can be achieved by first desiccating the embryos prior to flotation. Desiccation to no more than about 50% moisture content is very helpful. Preferably the embryos are desiccated about 15% moisture content or even somewhat less. Desiccation should proceed fairly rapidly to facilitate separation of the immature embryos from those that are sufficiently mature. Rapid desiccation stresses the immature embryos so that they generally become nonviable. This can be done by allowing the embryos to come to equilibrium moisture content when held for some time in atmospheres of constant relative humidity at moderate temperatures.

The method is most advantageously used with somatic embryos achieved by the techniques of plant tissue culture. It is particularly effective with somatic embryos of plants in the order Coniferales. This includes most of the important softwood species of both the northern and southern hemispheres.

It is an object of the present invention to provide a method for ordering plant embryos so that a specified end is essentially always oriented in a given direction.

It is another object to effect such ordering while also separating viable from nonviable embryos.

It is a further object to effect the ordering under conditions that minimize stress on the delicate embryos.

These and many other objects will become readily apparent to those skilled in the art upon reading the following detailed description taken in conjunction with the drawings.

BRIEF DESCRIPTION OF THE DRAWINGS

FIGS. 1 and 4 are elevation views, partially in section, of configurations of flotation containment vessels showing alternative embryo removal arrangements.

FIGS. 2 and 3 show details of venturi-like embryo removal systems using peripherally introduced fluid medium.

FIG. 5 is an overall diagrammatic view of the embryo orientation apparatus.

FIG. 6 is a sectional view of one arrangement for separation of oriented embryos from their transporting fluid.

FIG. 7 is a sectional view of a preferred configuration of an artificial seed.

DETAILED DESCRIPTION OF THE PREFERRED EMBODIMENTS

An understanding of the operation of the present invention can be readily gained by referring now to the drawings. FIG. 1 shows a preferred conical configuration of a containment vessel 2 containing an aqueous flotation medium 4. A side nipple 6 serves as a point for introduction of plant embryos suspended in a fluid medium 7. The introduction medium 7 is preferably of the same composition and at about the same temperature as the flotation medium 4.

While a conical configuration is generally preferred for the flotation containment vessel, other configurations such as an elongated vessel with sloping sides are also quite suitable. By making the upper portion of the vessel of lesser crosssectional area than the lower portion, the embryos, which are now properly oriented, are concentrated and more readily removed.

The embryos are introduced in a random configuration into the flotation containment vessel. Flotation medium 4 is adjusted in density so that it is barely higher than the density of viable embryos. Obviously, all fluid media which contacts the embryos must be of a benign, nonphytotoxic nature. All of the media may advantageously comprise a sterile sucrose solution, most usually in the range of 15%-25% concentration. This corresponds to a density at room temperature of about 1.059-1.104 g/cm$^3$. In the case of conifer embryos which have been partially desiccated, the concentration will preferably be in the range of about 18%-22% sucrose. The corresponding density range will be 1.072-1.090 g/cm$^3$. Many other materials beside sucrose can be used for formulating the flotation medium; e.g., other metabolizable or nonmetabolizable sugars with or without other added nutrient materials, sorbitol, xylitol, etc.

By partially or more completely desiccating the embryos before flotation, separation of viable from nonviable embryos is greatly enhanced. The immature or nonviable embryos cannot withstand the desiccation treatment. Very conveniently these have a density very slightly greater than the desiccated viable embryos. The density of the flotation solution can thus be adjusted so that the viable embryos will float and the nonviable embryos will sink. Preferably moisture content of the embryos is reduced to below 50% and most preferably to the range of 8-15%. The most preferred range will essentially be at equilibrium moisture for the ambient conditions.

Discrimination between viable and nonviable embryos generally exceeds 90% and often approaches 100%. This is indicated in FIGS. 1 and 4 by rising viable embryos 8 and sinking nonviable embryos 10 which accumulate at the bottom of the vessel. These latter embryos may be removed continuously or in batchwise fashion at convenient intervals.

The flotation medium must be essentially nonturbulent above and below the point of embryo introduction. This is of critical importance if the embryos are to assume their natural orientation of cotyledon end upward. While the embryos may be introduced in either batchwise or continuous fashion, this must be done without introducing significant turbulence into the flotation zone.

Referring to FIG. 1, at the top portion of the flotation containment vessel 2, an embryo transport fluid 12 is introduced through a plurality of manifolded peripheral inlets 14 having upturned nozzles 16. This sweeps the now oriented embryos 20 cotyledon end first into a conduit 18 where they are moved by fluid transport to a separation point. Conduit 18 should be of sufficiently small diameter, or the flow rate should be sufficiently great, so that the embryos can not turn end-for-end or otherwise lose their preferred orientation while being transported to the delivery point.

An alternative manifolded peripheral arrangement for transport medium introduction is shown in FIG. 3. Here a modified flotation containment vessel 22 has a plurality of inlets 24. These have upturned nozzles 26 formed in the wall of the containment vessel. In order to reduce uneven flow, the inlets should be arranged symmetrically around the neck portion of the vessel 2. Three such inlets have been found to be sufficient in most cases.

A further alternative arrangement for introduction of transport medium is shown in FIG. 4. Here, a modified flotation containment vessel 32 is provided with an axially located tube 34 which serves to introduce the transport medium 12 near the top of the vessel.

All of the constructions described for introduction of the transport medium may be considered venturi-like since the floating embryos move into a zone of higher velocity and lower pressure.

FIG. 5 shows the overall arrangement of one system that has proved to be very satisfactory. The embryos are suspended in the introduction medium 7 in a container 42. These are allowed to flow by gravity or otherwise introduced into the flotation containment vessel 2 through nipple 6. Immediately after introduction all of the embryos may initially sink. However, shortly thereafter the viable embryos will begin their rise to the upper zone of the flotation medium. After flotation, the selected embryos, now oriented cotyledon end upward, are removed through conduit 18 to a separation mechanism shown generally at 44. The fluid transport medium after separation of the embryos is recycled through tubing 46 and pump 50. The repressurized medium from the pump 50 flows through tubing 48 into manifold 52. From there it is directed to the manifolded peripheral inlets 14. Pump 50 may be any suitable low head, low volume pump, such as a peristaltic pump. Conditions must be such that sterility of the transporting medium is maintained if it is recycled. Any overflow fluid can be redirected to vessel 42 containing the unsorted, unoriented embryos.

One form of suitable embryo separation mechanism 44 is seen in FIG. 6. The terminal end of conduit 18 enters a separation head 62, seen here in cross section. A moving porous belt pair having a narrow lower belt 68 and narrow upper belt 70 are fed in opposing relationship through separation head 62. Each of the belts is supported by driven pulleys 72 and idling pulleys 74. At a point downstream from the termination of conduit 18, a screened orifice 66 leads to a side nipple 64 where transport fluid medium 12 is drawn off for recycle. The freed embryos 76, now still cotyledon end first and generally singulated in end-to-end fashion, are discharged from between the belt pairs 68, 70 where they may be handled by robotic or other means for further processing.

From the discharge point of the separation head the embryos will normally be converted into artificial seeds for planting as nursery stock. A preferred type of artificial seed 80 for conifer somatic embryos is shown in FIG. 7. An outer covering 82, analogous to a protective natural seed coat, is closed at one end and open at the other. This is preferably made of a biodegradable product, such as water resistant paper, but may also be of a thin walled plastic material. A porous inner tube 84, positioned axially within the outer covering 82, holds the embryo. Inner tube 84 is also closed at one end. This may be made of paper but is more preferably formed of a very thin walled plaster-of-Paris casting. The somatic embryo 76 is inserted cotyledon end first into the inner tube.

The bulk of the inner portion of the artificial seed is filled with a nutrient gel 86 which serves as an artificial gametophyte for the germinating embryo. Inner tube 84 is sized so that the cotyledon end of the embryo 76 is in contact with the porous inner tube walls in order to absorb nutrients from the gel.

The open end of the outer shell 82 is sealed with a wax plug 88. This does not cover the end of inner tube 84, however. After the embryo 76 has been inserted the artificial seed may be further sealed by a thin wax layer 90 to prevent moisture loss and preserve sterility.

EXAMPLE

Douglas-fir embryos were desiccated by placing them over a saturated solution of $Ca(NO_3)_2 \cdot 4H_2O$ for 5–7 days during which time they came to an equilibrium moisture content below 15%. Relative humidity over this solution is about 54%. Prior to desiccation the embryos were hand selected into categories regarded as mature and immature. In a four times replicated experiment a mixture of 15 embryos believed to be mature and 15 believed to be immature were introduced batchwise into a 1 L Erlenmeyer flask configured as shown in FIG. 1. The flotation medium and the medium in which the embryos were suspended when introduced was a 20% sucrose solution having a density of 1.081 g/cm$^3$. The transport medium, also a 20% sucrose solution, was turned on into the peripheral jets at the top of the flask and the embryos were carried cotyledon end first into the delivery conduit which was made of flexible tubing 2.0 mm in inside diameter. Of the 180 total embryos regarded as mature, 166 or 92% floated and were considered as accepted. Of these 163, or 98%, of the accepted embryos were delivered cotyledon end first. Only 8 of the 180 embryos (4%) regarded as immature floated and of these 5 were oriented cotyledon end first.

Germination tests, using an agar gelled germination medium, showed that nearly all of the accepted embryos germinated into apparently normal plantlets. Only a very small number of the rejected embryos germinated and, of these, most did not form normal plantlets.

The invention having thus been described in the best modes known to the inventors, it will be evident to those skilled in the art that many variations could be made in the method and apparatus described without departing from the spirit of the invention. Thus, the invention should be considered as limited only by the scope of the appended claims.

We claim:

1. A method for directionally orienting a multiplicity of plant embryos, said embryos being bipolar with a cotyledon end and a radicle end, which comprises:

introducing said embryos into a low turbulence, nonphytotoxic fluid aqueous flotation medium of uniform density and of a higher density than that of the embryos to be oriented so that the embryos to be oriented will float, said flotation medium having a lower region and an upper region and being in a containment vessel, said embryos being introduced into the lower region of the flotation medium in the vessel;

retaining the embryos in the flotation medium for a sufficient time to permit the embryos to assume a cotyledon end upward orientation as said embryos float to the upper region of the flotation medium;

capturing and entraining the cotyledon end upward oriented embryos in the upper region of the flotation medium in a flowing transport medium of increased velocity so that the embryos are swept cotyledon end first into a conduit in order to remove them from the body of flotation medium;

transporting the oriented embryos in the flowing transport medium in the conduit to a delivery point while maintaining a cotyledon end first orientation; and separating the embryos from the transport medium at the delivery point in a manner whereby the cotyledon end first orientation is maintained, so that the separated embryos can be further processed.

2. The method of claim 1 whereby the containment vessel is of gradually decreasing cross-sectional area from bottom to top so that the concentration of oriented embryos per unit volume of flotation medium is increased.

3. The method of claim 2 in which the containment vessel is of generally conical configuration.

4. The method of claims 2 or 3 in which the embryos are introduced into the flotation medium in the containment vessel while suspended in a fluid introduction medium of essentially identical composition to the flotation medium.

5. The method of claim 4 in which the embryos are introduced in batchwise fashion.

6. The method of claim 4 in which the embryos are introduced continuously so as to create a gentle nonturbulent upward flow of flotation medium and floating embryos, the flow velocity of said flotation medium thereby increasing toward the upper region of the containment vessel.

7. The method of claims 1 or 2 in which the oriented embryos are swept into the conduit and entrained in the flowing transport medium by venturi-like action adjacent the top of the container.

8. The method of claim 3 in which the oriented embryos are swept into the conduit and entrained in the flowing transport medium by venturi-like action adjacent the top of the container.

9. The method of claim 8 in which the venturi-like action is created by injecting transport medium into the flotation medium adjacent the apex of the cone, said medium being injected upward in the direction of travel of the rising embryos so as to increase localized fluid velocity and sweep the embryos into the conduit.

10. The method of claim 9 in which the transport medium is injected into the solution peripherally around the cone apex.

11. The method of claim 9 in which the transport medium is injected into the solution axially adjacent the cone apex.

12. The method of claim 1 in which the transport medium is essentially identical in composition to that of the flotation medium in the containment vessel.

13. The method of claim 12 in which the transport medium separated from the embryos at the delivery point is recycled as embryo introduction medium or transport medium.

14. The method of claim 1 in which the embryos are somatic embryos.

15. The method of claim 14 in which the embryos are first dried to a maximum of 50% moisture content.

16. The method of claim 15 in which the embryos are dried to less than about 15% moisture content.

17. The method of claim 14 in which the embryos are members of species within the order Coniferales.

18. The method of claim 1 in which the flotation medium is a sucrose solution in the range of about 15-25% concentration.

19. The method of claim 18 in which the sucrose solution is in the range of about 18-22% concentration.

20. The method of claim 1 in which the density of the flotation medium is within the range of about 1.059-1.104 g/cm$^3$.

21. The method of claim 20 in which the density of the flotation medium is within the range of about 1.072-1.090 g/cm$^3$.

22. The method of claims 1, 14, 15, 16, or 17 in which the density of the flotation medium is adjusted so that nonviable and immature embryos will sink while viable embryos will float.

23. The method of claim 1 in which further includes inserting the separated embryos cotyledon end first into artificial seeds.

* * * * *